US012802217B2

(12) United States Patent
Okaya et al.

(10) Patent No.: US 12,802,217 B2

(45) Date of Patent: Nov. 17, 2026

(54) MEDICAL IMAGE PROCESSING DEVICE, TREATMENT SYSTEM, MEDICAL IMAGE PROCESSING METHOD, AND STORAGE MEDIUM

(71) Applicants: TOSHIBA ENERGY SYSTEMS & SOLUTIONS CORPORATION, Kawasaki (JP); National Institutes for Quantum Science and Technology, Chiba (JP)

(72) Inventors: Keiko Okaya, Tokyo (JP); Yasuhiro Soekawa, Tokyo (JP); Yasushi Iseki, Yokohama Kanagawa (JP); Shinichiro Mori, Chiba (JP)

(73) Assignees: TOSHIBA ENERGY SYSTEMS & SOLUTIONS CORPORATION;, Kawasaki (JP); NATIONAL INSTITUTES FOR QUANTUM SCIENCE AND TECHNOLOGY, Chiba (JP)

( * ) Notice: Subject to any disclaimer, the term of this patent is extended or adjusted under 35 U.S.C. 154(b) by 202 days.

(21) Appl. No.: 18/770,331

(22) Filed: Jul. 11, 2024

(65) Prior Publication Data

US 2024/0362783 A1 Oct. 31, 2024

Related U.S. Application Data

(63) Continuation of application No. PCT/JP2023/005223, filed on Feb. 15, 2023.

(30) Foreign Application Priority Data

Mar. 16, 2022 (JP) ................................ 2022-041522

(51) Int. Cl.

*G06T 7/00* (2017.01)
*A61B 5/00* (2006.01)

(Continued)

(52) U.S. Cl.

CPC .............. *G06T 7/0012* (2013.01); *A61B 5/70* (2013.01); *G06F 3/14* (2013.01); *G06T 15/00* (2013.01); *G06T 2207/10121* (2013.01)

(58) Field of Classification Search

CPC .................. G06T 7/0012; G06T 15/00; G06T 2207/10121; A61B 5/70; G06F 3/14

See application file for complete search history.

(56) References Cited

U.S. PATENT DOCUMENTS 8,737,708 B2 * 5/2014 Hartmann .............. A61B 34/20 382/128
11,231,787 B2 * 1/2022 Isaacs ...................... H04N 7/18

(Continued)

FOREIGN PATENT DOCUMENTS

JP 2018-042831 A 3/2018
JP 2018-507073 A 3/2018

(Continued)

OTHER PUBLICATIONS

International Search Report with English Translation in corresponding International Application No. PCT/JP2023/005223, dated Apr. 11, 2023.

*Primary Examiner* — Gregory M Desire

(74) *Attorney, Agent, or Firm* — Foley & Lardner LLP

(57) ABSTRACT

A medical image processing device according to an embodiment has a first image acquirer, a second image acquirer, a 3D-3D positioning executer, and a display controller. The first image acquirer acquires a first three-dimensional fluoroscopic image that is a three-dimensional fluoroscopic image of a patient. The second image acquirer acquires a second three-dimensional fluoroscopic image that is a three-dimensional fluoroscopic image of the patient. The 3D-3D positioning executer calculates a first shift amount between the first three-dimensional fluoroscopic image and the second three-dimensional fluoroscopic image. The display con- (Continued)

troller causes the display device to display a first DRR image generated from the second three-dimensional fluoroscopic image corrected based on the first shift amount, and a two-dimensional fluoroscopic image of the patient.

9 Claims, 8 Drawing Sheets

(51) Int. Cl.
*G06F 3/14* (2006.01)
*G06T 15/00* (2011.01)

(56) References Cited

U.S. PATENT DOCUMENTS

| | | | | |
|---|---|---|---|---|
| 11,399,895 | B2 * | 8/2022 | Soper | A61B 34/20 |
| 12,310,770 | B2 * | 5/2025 | Benseghir | A61B 6/12 |
| 2017/0340902 | A1 | 11/2017 | Vilsmeier et al. | |
| 2018/0197303 | A1 | 7/2018 | Jordan et al. | |
| 2018/0280727 | A1 | 10/2018 | Takahashi et al. | |

FOREIGN PATENT DOCUMENTS

| | | | |
|---|---|---|---|
| JP | 6611814 | B2 | 11/2019 |
| JP | 2020-503148 | A | 1/2020 |
| WO | WO-2018/051557 | A1 | 3/2018 |

* cited by examiner

MEDICAL IMAGE PROCESSING DEVICE, TREATMENT SYSTEM, MEDICAL IMAGE PROCESSING METHOD, AND STORAGE MEDIUM

CROSS-REFERENCE TO RELATED APPLICATION

The present application claims priority based on Japanese Patent Application No. 2022-041522 filed Mar. 16, 2022 and PCT/JP2023/005223 filed Feb. 15, 2023, the contents of which are incorporated herein by reference.

FIELD

Embodiments of the present invention relate to a medical image processing device, a treatment system, a medical image processing method, and a storage medium.

BACKGROUND

Radiation therapy is a treatment method for destroying a lesion in a body of a patient by irradiating the lesion with radiation. In this case, it is necessary for radiation to be accurately radiated to a position of the lesion. This is because a normal tissue inside a body of the patient may be influenced when the normal tissue is irradiated with the radiation. To this end, when the radiation therapy is performed, first, computed tomography (CT) is performed in advance and a position of the lesion in the body of the patient is ascertained in three dimensions in a treatment planning stage. A direction of radiation irradiation or intensity of the irradiation radiation is planned to reduce irradiation toward normal tissue, based on the ascertained position of the lesion. Thereafter, in a treatment stage, a position of the patient is matched with that of the patient in the treatment planning stage, and the lesion is irradiated with radiation according to an irradiation direction or irradiation intensity planned in the treatment planning stage.

In aligning the patient in the treatment stage, three-dimensional CT data is virtually disposed in a treatment room, and a position of a movable bed in the treatment room is adjusted so that a position of the patient actually laid on a bed matches a position of the three-dimensional CT data. More specifically, two images including a three-dimensional CT image of the patient captured in a state where the patient lies on the bed and a three-dimensional CT image captured at the time of treatment planning are collated (3D-3D positioning) so that a deviation in a position of the patient between the two images is obtained. The bed is moved based on the deviation in the position of the patient obtained through the image collation, and a position of a lesion or bone inside a body of the patient is aligned with that at the time of the treatment plan. Thereafter, two images including an X-ray fluoroscopic image of the inside of the body of the patient captured in a state where the patient lies on the bed and a digitally reconstructed radiograph (DRR) image obtained by virtually reconstructing the X-ray fluoroscopic image from the 3D CT image captured at the time of treatment planning are compared or collated with each other (3D-2D positioning) when necessary, positioning is approved, and the lesion is irradiated with radiation.

However, in the related art, since a DRR image reconstructed from the 3D CT image captured at the time of treatment planning is generally collated with the X-ray fluoroscopic image, the CT image captured in the treatment stage may not be effectively utilized for positioning of the patient in some cases.

DETAILED DESCRIPTION

Hereinafter, a medical image processing device, a treatment system, a medical image processing method, and a storage medium of the embodiment will be described with reference to the drawings.

A medical image processing device according to an embodiment includes a first image acquirer, s second image acquirer, a 3D-3D positioning executer, and a display controller. The first image acquirer acquire a first three-dimensional fluoroscopic image, the first three-dimensional fluoroscopic image being a three-dimensional fluoroscopic image of a patient captured in a first stage. The second image acquirer acquires a second three-dimensional fluoroscopic image, the second three-dimensional fluoroscopic image being a three-dimensional fluoroscopic image of the patient captured in a second stage after the first stage. The 3D-3D positioning executer executes 3D-3D positioning for calculating a first shift amount between the first three-dimensional fluoroscopic image and the second three-dimensional fluoroscopic image. The display controller causes the display device to display a first DRR image generated from the second three-dimensional fluoroscopic image corrected based on the first shift amount, and a two-dimensional fluoroscopic image of the patient.

[Overall Configuration]

Figure 1:
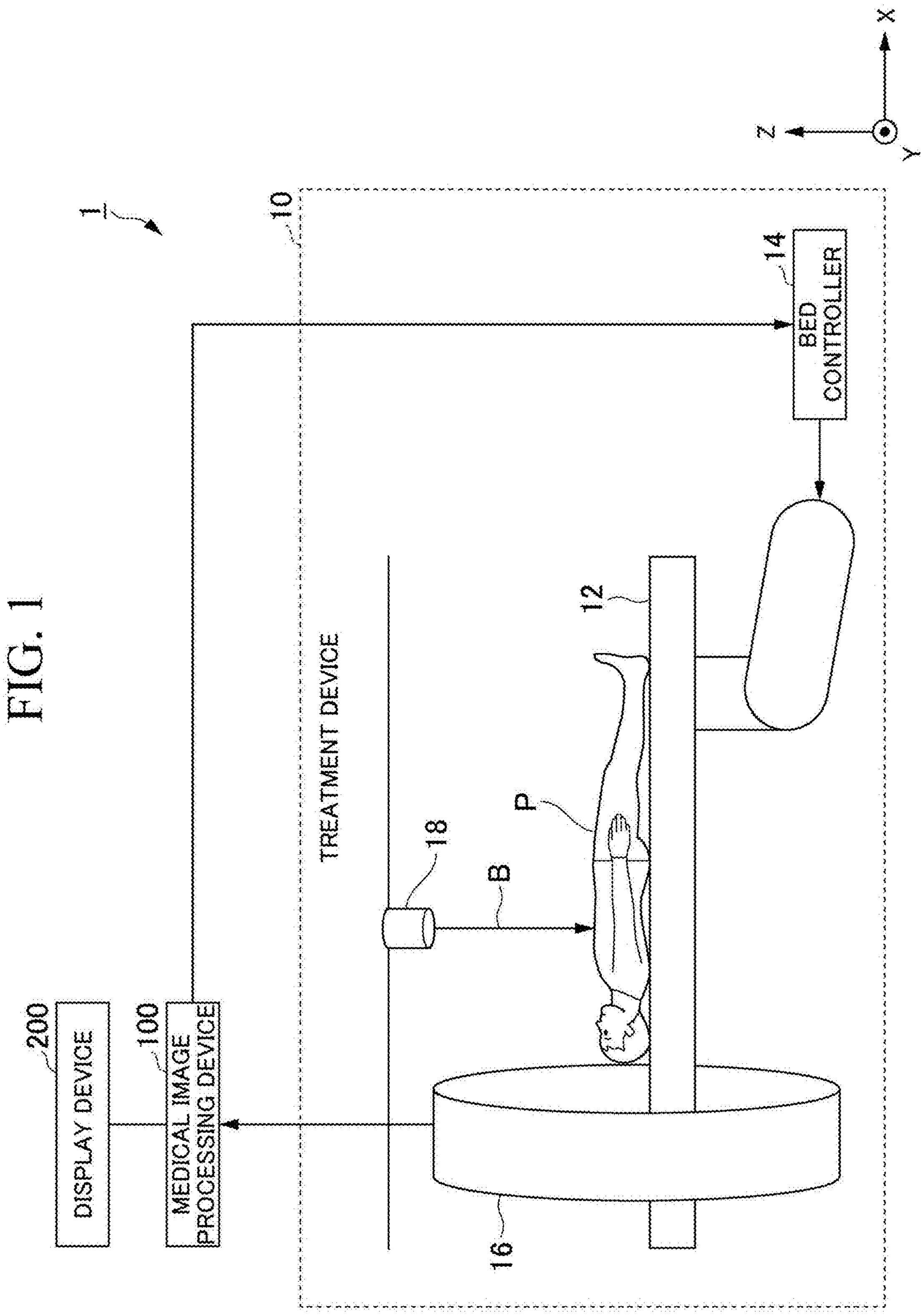
FIG. 1 is a block diagram showing a schematic configuration of a treatment system including a medical image processing device 100 of the embodiment.

FIG. 1 is a block diagram showing a schematic configuration of a treatment system including a medical image processing device 100 of an embodiment. The treatment system 1 includes, for example, a treatment device 10, a medical image processing device 100, and a display device 200. The treatment device 10 includes, for example, a bed 12, a bed controller 14, a computed tomography (CT) device 16 (hereinafter referred to as a “CT photographing device 16”), and a treatment beam irradiation gate 18.

The bed 12 is a movable treatment table that fixes a subject (patient) P who receives treatment using radiation, for example, in a laid state by a fixing tool or the like. The bed 12 moves in a state where the patient P is fixed inside the annular CT photographing device 16 having an opening according to the control of the bed controller 14. The bed controller 14 controls a translation mechanism and a rotation mechanism provided in the bed 12 to align a position of the patient to an irradiation position according to a movement amount signal output from the medical image processing device 100. The translation mechanism can drive the bed 12 in three axial directions, and the rotation mechanism can rotate the bed 12 around three axes. That is, the bed controller 14 controls, for example, the translation mechanism and the rotation mechanism of the bed 12 to move the bed 12 with six degrees of freedom. A degree of freedom at which the bed controller 14 controls the bed 12 may not be the six degrees of freedom, and may be a degree of freedom (for example, four degrees of freedom) lower than the six degrees of freedom or a degree of freedom (for example, eight degrees of freedom) higher than the six degrees of freedom. The bed 12 is installed to be able to be moved to both a position where photographing using the CT photographing device 16 is executed and a position where irradiation of a treatment beam B using the treatment beam irradiation gate 18 is performed when the positions are different.

The CT photographing device 16 is an imaging device for performing three-dimensional computed tomography. The CT photographing device 16 includes a plurality of radiation sources disposed inside a circular (gantry) opening, and radiates radiation for seeing through the inside of the body of the patient P from each radiation source. That is, the CT photographing device 16 radiates the radiation from a plurality of positions around the patient P. The radiation radiated from each radiation source in the CT photographing device 16 is, for example, X-rays. The CT photographing device 16 detects the radiation irradiated from the corresponding radiation source, passing through the inside of the body of the patient P, and reaching a plurality of radiation detectors disposed inside the circular opening using the radiation detectors. The CT photographing device 16 generates a CT image of the inside of the body of the patient P based on the magnitude of the energy of the radiation detected by each radiation detector. The CT image of the patient P generated by the CT photographing device 16 is a three-dimensional digital image in which a magnitude of a degree of radiation attenuation at each location inside the body is expressed as a digital value. The CT photographing device 16 outputs the generated CT image to the medical image processing device 100. The photography of the inside of the body of the patient P in the CT photographing device 16, that is, the irradiation of the radiation from each radiation source or the generation of the CT image based on the radiation detected by each radiation detector is controlled, for example, by a photography controller (not shown). The CT photographing device 16 is an example of a "first imaging device".

The treatment beam irradiation gate 18 irradiates radiation for destroying a tumor (lesion), which is a treatment target site present in the body of the patient P, as the treatment beam B. The treatment beam B is, for example, an X-ray, a y ray, an electron beam, a proton beam, a neutron beam, or a heavy particle beam. The treatment beam B is radiated linearly from the treatment beam irradiation gate 18 to the patient P (more specifically, a tumor in the body of the patient P). The irradiation of the treatment beam B at the treatment beam irradiation gate 18 is controlled by, for example, a treatment beam irradiation controller (not shown). In the treatment system 1, the treatment beam irradiation gate 18 is an example of an "irradiator."

In the radiation therapy, the treatment plan is made in a situation in which a treatment room is simulated. That is, in the radiation therapy, an irradiation direction, intensity, or the like when the patient P is irradiated with the treatment beam B is planned through a simulation of a state where the patient P is laid on the bed 12 in the treatment room. Specifically, an irradiation target location is specified by a doctor for the CT image, or such processing is performed automatically. To this end, information such as a parameter representing an angle of the bed 12 or a body position (such as lying on one's back or face down) of the patient in the treatment room is assigned to the CT image at a treatment planning stage. This is also true for the CT image captured immediately before the radiation therapy or the CT image captured at the time of previous radiation therapy. That is, the parameter representing the angle of the bed 12 or the body position of the patient at the time of photographing is assigned to the CT image obtained by photographing the inside of the body of the patient P using the CT photographing device 16.

FIG. 1 shows a configuration of the treatment device 10 including the CT photographing device 16 and one fixed treatment beam irradiation gate 18, but the configuration of the treatment device 10 is not limited to the above-described configuration. For example, the treatment device 10 may be configured to include a CT photographing device having a configuration in which a set of a radiation source and a radiation detector rotate inside the circular opening, and a photographing device that generates a three-dimensional image of the inside of the body of the patient P, such as a cone-beam (CB) CT device, a magnetic resonance imaging (MRI) device, or an ultrasonic diagnostic device, instead of the CT photographing device 16. For example, the treatment device 10 may be configured to further include a plurality of treatment beam irradiation gates, such as a treatment beam irradiation gate that irradiates the patient P with a treatment beam in a horizontal direction. For example, the treatment device 10 may be configured to irradiate the patient P with a treatment beam from various directions by rotating around the patient P, such as rotating one treatment beam irradiation gate 18 shown in FIG. 1 360 degrees around a rotation axis in a horizontal direction X shown in FIG. 1. For example, the treatment device 10 may be configured to include one or a plurality of photographing devices configured of a pair of a radiation source and a radiation detector instead of the CT photographing device 16, and the photographing device may be configured to rotate 360 degrees around the rotation axis in the horizontal direction X shown in FIG. 1 to photograph the inside of the body of the patient P from various directions. This configuration is called a rotating gantry type treatment device. In this case, for example, one treatment beam irradiation gate 18 shown in FIG. 1 may be configured to rotate simultaneously around the same rotation axis as the photographing device. Furthermore, in FIG. 1, the CT photographing device 16 and the treatment beam irradiation gate 18 are installed at close positions, but the CT photographing device 16 and the treatment beam irradiation gate 18 may be installed at positions apart from each other, and the positions of the CT photographing device 16 and the treatment beam irradiation gate 18 may be movable relative to each other by the bed 12 on which the patient P is laid.

The medical image processing device 100 outputs the movement amount signal for moving the bed 12 to the bed controller 14 to align the position of the patient P to the same body position as in the time of the treatment plan. That is, the medical image processing device 100 outputs to the bed controller 14 a movement amount signal for moving the patient P to a position and at a posture where a tumor or tissue to be treated can be appropriately irradiated with the treatment beam B in the radiation therapy.

The display device 200 displays images for presenting various types of information in the treatment system 1 to a radiation therapist (such as a doctor) who uses the treatment system 1, including during positioning of the patient P in the medical image processing device 100. The display device 200 displays various images such as the CT image or X-ray fluoroscopic image output by the medical image processing device 100, or an image obtained by superimposing various types of information on these images. Here, examples of the various types of information include patient information (age, sex, height, weight, or the like), image capturing conditions (photographing part, presence or absence of a contrast agent, tube voltage, tube current, or the like), image capturing date and time, and the body position of the patient (head-up position, feet-up position, or the like). The display device 200 is, for example, a display device such as a liquid crystal display (LCD). The radiation therapist can obtain information when the radiation therapy is performed using the treatment system 1 by visually confirming the image displayed on the display device 200. The treatment system 1 may be configured to include a user interface such as an operator (not shown) operated by the radiation therapist, and to allow various functions executed by the treatment system 1 to be manually operated.

Figure 2:
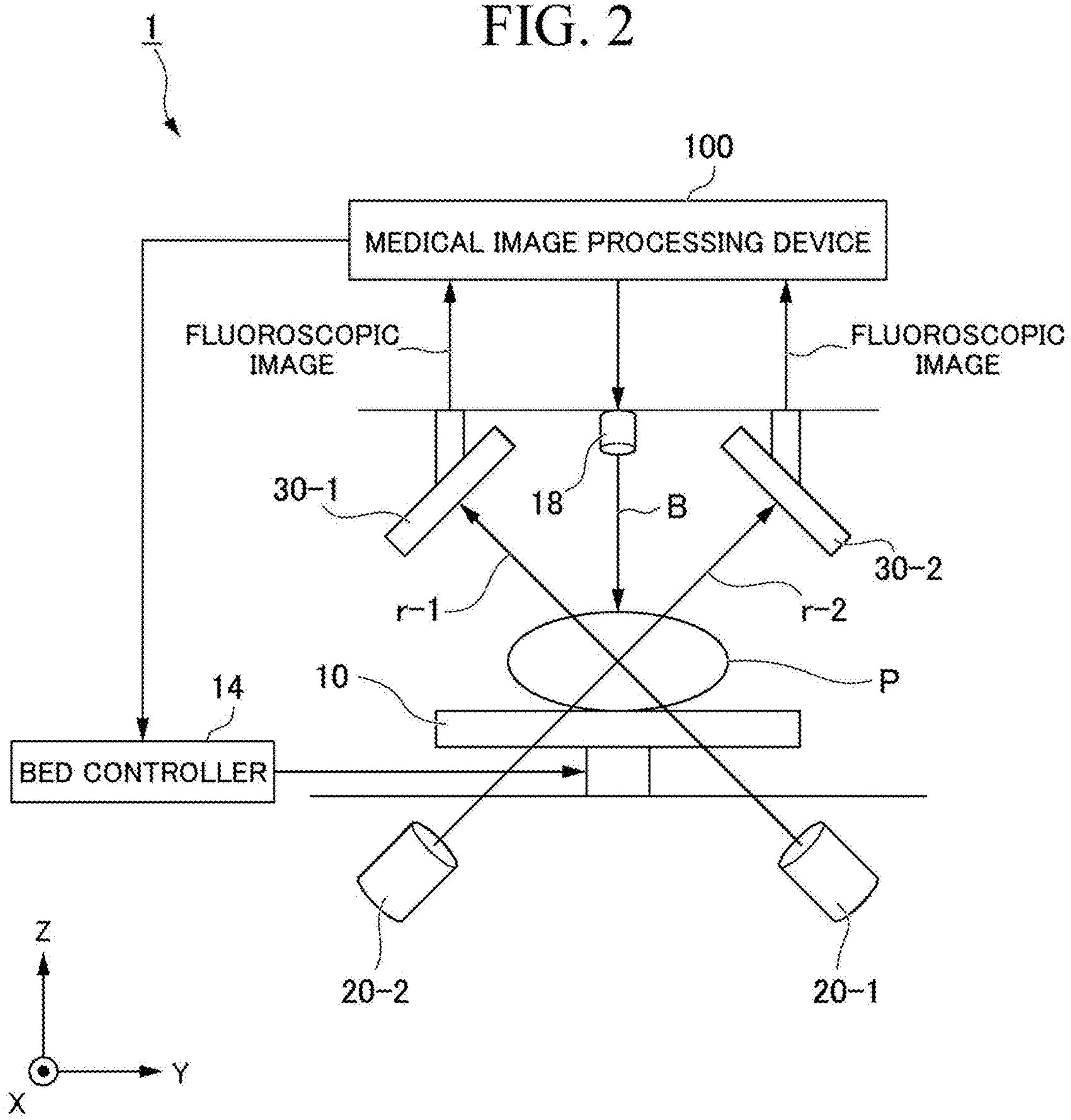
FIG. 2 is a block diagram showing a schematic configuration of a treatment system including the medical image processing device 100 of the embodiment from an angle different from that of FIG. 1.

FIG. 2 is a block diagram showing a schematic configuration of a treatment system including the medical image processing device 100 according to the embodiment from an angle different from that shown in FIG. 1. In addition to the configuration shown in FIG. 1, the treatment system 1 includes, for example, two radiation sources 20 (a radiation source 20-1 and a radiation source 20-2) and two radiation detectors 30 (a radiation detector 30-1 and a radiation detector 30-2).

The radiation source 20-1 radiates radiation r-1 for seeing through the inside the body of the patient P from a predetermined angle. The radiation source 20-2 radiates radiation r-2 for seeing through the inside the body of the patient P from a predetermined angle different from that of the radiation source 20-1. The radiation r-1 and the radiation r-2 are, for example, X-rays. FIG. 1 shows a case where X-ray photography is performed on the patient P fixed on the bed 12 from two directions. In FIG. 1, a controller that controls the radiation of the radiation r in the radiation source 20 is omitted.

The radiation detector 30-1 detects the radiation r-1 radiated from the radiation source 20-1, passing through the inside of the body of the patient P, and reaching the radiation detector 30-1, and generates an X-ray fluoroscopic image of the inside of the body of the patient P according to a magnitude of energy of the detected radiation r-1. The radiation detector 30-2 detects the radiation r-2 radiated from the radiation source 20-2 and passing through the inside of the body of the patient P, and generates an X-ray fluoroscopic image of the inside of the body of the patient P according to a magnitude of energy of the detected radiation r-2. The radiation detector 30 includes X-ray detectors disposed in a two-dimensional array, and generates a digital image in which the magnitude of the energy of the radiation r that reaches each X-ray detector is expressed as a digital value, as the X-ray fluoroscopic image. The radiation detector 30 is, for example, a flat panel detector (FPD), an image intensifier, or a color image intensifier. In the following description, each radiation detector 30 is assumed to be an FPD. The radiation detector 30 (FPD) outputs each generated X-ray fluoroscopic image to the medical image processing device 100. In FIG. 1, a controller that controls the generation of the X-ray fluoroscopic image in the radiation detector 30 is not shown. A combination of the radiation source 20 and the radiation detector 30 is an example of a "second imaging device."

FIG. 2 shows a configuration in which the treatment system 1 includes two sets of the radiation source 20 and the radiation detector 30. However, the number of combinations of the radiation source 20 and the radiation detector 30 included in the treatment system 1 is not limited to two. For example, the treatment system 1 may include three or more sets of the radiation source 20 and the radiation detector 30. The treatment system 1 may also include only one photographing device (one set of radiation source 20 and radiation detector 30). Hereinafter, the combination of radiation source 20 and radiation detector 30 may be referred to as an "X-ray photographing device."

The various components shown in FIGS. 1 and 2 may be connected to each other by wires, or may be connected wirelessly, for example, via a local area network (LAN) or a wide area network (WAN).

[Medical Image Processing Device]

Figure 3:
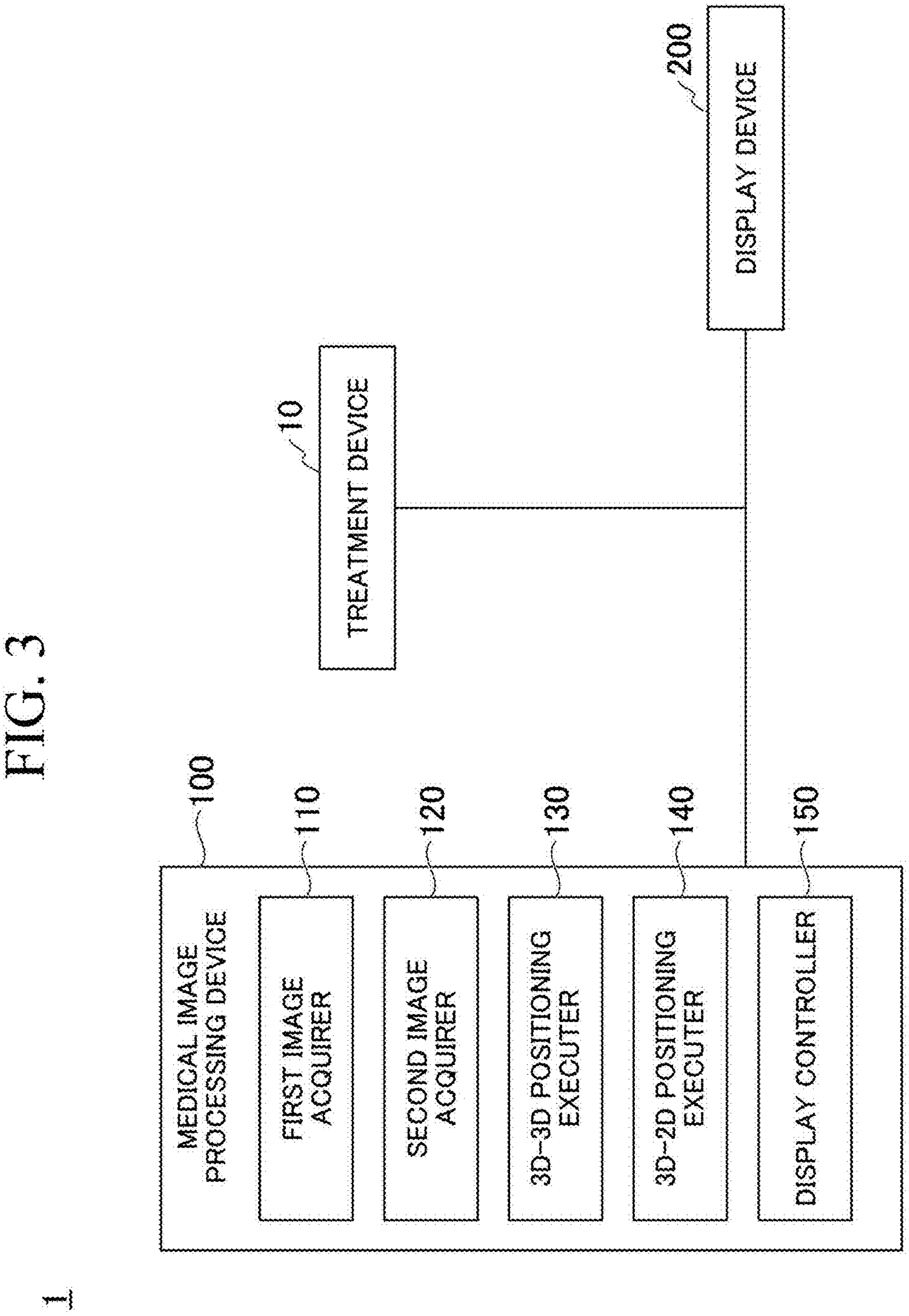
FIG. 3 is a block diagram mainly showing a schematic configuration of the medical image processing device 100 of the embodiment.

Hereinafter, the medical image processing device 100 of the embodiment will be described. FIG. 3 is a block diagram mainly showing a schematic configuration of the medical image processing device 100 of the embodiment. The medical image processing device 100 includes, for example, a first image acquirer 110, a second image acquirer 120, a 3D-3D positioning executer 130, a 3D-2D positioning executer 140, and a display controller 150.

Some or all of components of the medical image processing device 100 are realized by, for example, a hardware processor such as a central processing unit (CPU) executing a program (software). Some or all of these components may be realized by hardware (circuit; including circuitry) such as a large scale integration (LSI), an application specific integrated circuit (ASIC), a field-programmable gate array (FPGA), or a graphics processing unit (GPU), or may be realized by collaboration between software and hardware. Some or all of functions of these components may be realized by a dedicated LSI. The program may be stored in a storage device (a storage device including a non-transitory storage medium) such as a read only memory (ROM), a random access memory (RAM), a hard disk drive (HDD), or a flash memory included in the medical image processing device 100 in advance, or may be stored in a removable storage medium (non-transitory storage medium) such as a DVD or CD-ROM and installed in the HDD or flash memory included in the medical image processing device 100 when the storage medium is mounted on a drive device included in the medical image processing device 100. The program may be downloaded from another computer device via a network and installed in the HDD or flash memory included in the medical image processing device 100.

The first image acquirer 110 acquires a first image regarding the patient P before treatment and parameters (and/or treatment plan data) associated with the first image. The first image is, for example, a three-dimensional CT image representing a three-dimensional shape of the inside of the body of the patient P, which is photographed by the CT photographing device 16 in the treatment planning stage when the radiation therapy is performed. The first image is used for a determination of a direction (a path including an inclination, a distance, or the like) or intensity of the treatment beam B to be radiated to the patient P in the radiation therapy. The first image is an example of a "first three-dimensional fluoroscopic image."

The second image acquirer 120 acquires a second image of the patient P immediately before the start of the radiation therapy and parameters associated with the second image. The second image is, for example, a three-dimensional CT image representing the three-dimensional shape of the inside of the body of the patient P photographed by the CT photographing device 16 in order to align the body position of the patient P at the time of irradiation with the treatment beam B in the radiation therapy (that is, to perform positioning). That is, the second image is an image captured by the CT photographing device 16 immediately before the treatment beam B is radiated from the treatment beam irradiation gate 18. In this case, the first image and the second image are captured at different times, but methods of capturing the image are the same. The second image is an example of a "second three-dimensional fluoroscopic image."

The 3D-3D positioning executer 130 performs 3D-3D positioning processing for aligning the position of the patient P when the radiation therapy is performed, based on the first image acquired by the first image acquirer 110 and the second image acquired by the second image acquirer 120. More specifically, for example, the medical image processing device 100 calculates a three-dimensional shift amount (hereinafter referred to as a "first shift amount" in some cases) between the first image acquired by the first image acquirer 110 and the second image acquired by the second image acquirer 120, and aligns the positions between the first image and the second image by correcting the second image by the calculated first shift amount. In this case, the medical image processing device 100 may output a movement amount signal for moving the bed 12 on which the patient is laid and fixed, by the first shift amount to the bed controller 14, and the bed controller 14 may move the bed 12 by the first shift amount. Furthermore, when the CT photographing device 16 and the treatment beam irradiation gate 18 are installed at positions apart from each other, the medical image processing device 100 may output a movement amount signal for moving the bed 12 by an amount obtained by adding the first shift amount to a distance between the CT imaging position and the irradiation position to the bed controller 14, and the bed controller 14 may move the bed 12 by the amount obtained by adding the first shift amount to the distance.

Figure 4:
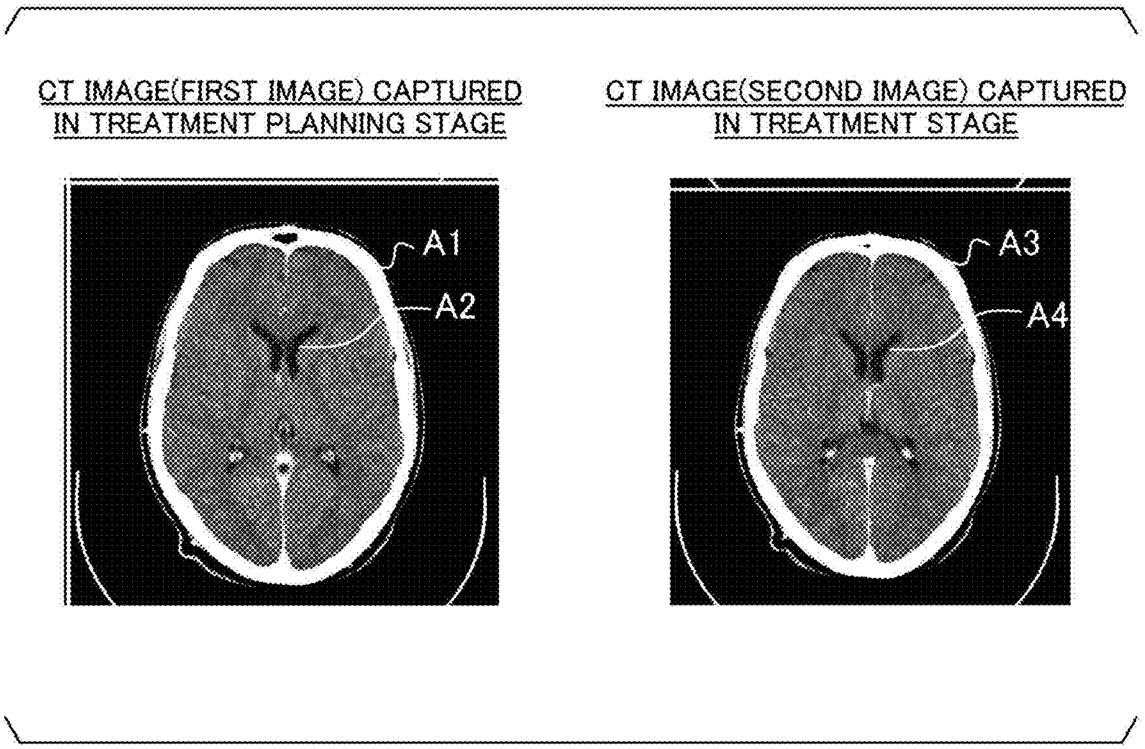
FIG. 4 is a diagram showing an overview of 3D-3D positioning processing that is executed by a 3D-3D positioning executer 130.

FIG. 4 is a diagram showing an overview of the 3D-3D positioning processing that is executed by the 3D-3D positioning executer 130. A left part of FIG. 4 shows a CT image (that is, the first image) captured in the treatment planning stage (an example of a "first stage"), and a right part of FIG. 4 shows a CT image (that is, the second image) captured in the treatment stage (an example of a "second stage"). In FIG. 4, reference sign A1 indicates a photographed skull in the first image, reference sign A2 indicates a photographed anterior horn of a lateral ventricle in the first image, reference sign A3 indicates the photographed skull in the second image, and reference sign A4 indicates a photographed anterior horn of a lateral ventricle in the second image.

In the related art, generally, when positioning of the patient is performed in the radiation therapy, a DRR image generated from a CT image captured in the treatment planning stage is collated with an X-ray fluoroscopy image captured in the treatment stage (3D-2D positioning), and the bed 12 is moved by the specified shift amount so that positioning is performed. On the other hand, as shown in FIG. 4, the CT image includes position information regarding a space such as an anterior horn of a lateral ventricle or internal organs, in addition to position information regarding a bone part such as a skull, unlike the X-ray fluoroscopy image. Therefore, it is possible to perform the positioning more accurately by performing the 3D-3D positioning processing in the 3D-3D positioning executer 130.

The 3D-2D positioning executer 140 executes the 3D-2D positioning processing for collating the DRR image generated from the second image with the X-ray fluoroscopic image of the patient captured in the treatment stage. More specifically, the 3D-2D positioning executer 140 calculates a three-dimensional shift amount (hereinafter referred to as a "second shift amount" in some cases) between the DRR image generated from the second image corrected by the first shift amount and the X-ray fluoroscopic image of the patient captured after the bed 12 on which the patient is laid and fixed is moved by the first shift amount. For example, when the calculated second shift amount is smaller than a threshold value, the radiation therapist approves the positioning. On the other hand, when the calculated second shift amount is equal to or larger than the threshold value, the bed controller 14 moves the bed 12 by the calculated second shift amount, and captures the X-ray fluoroscopic image of the patient again, and the 3D-2D positioning executer 140 executes the 3D-2D positioning processing again using the captured X-ray fluoroscopic image. The processing is repeated, and finally, the positioning is approved by the radiation therapist.

The 3D-2D positioning executer 140 is also configured to execute the 3D-2D positioning processing for collating the DRR image generated from the first image with the X-ray fluoroscopic image of the patient, in addition to the 3D-2D positioning processing for collating the DRR image generated from the second image with the X-ray fluoroscopic image of the patient. More specifically, the 3D-2D positioning executer 140 calculates a three-dimensional shift amount (hereinafter referred to as a "third shift amount" in some cases) between the DRR image generated from the first image and the captured X-ray fluoroscopic image of the patient. In this case, the captured X-ray fluoroscopic image of the patient may be an image captured after the bed 12 is moved by the first shift amount as described above, or may be an image captured after the bed 12 is moved by an amount obtained by adding the first shift amount to the distance between the CT imaging position and the irradiation position when the CT photographing device 16 and the treatment beam irradiation gate 18 are installed at positions apart from each other. The radiation therapist approves the positioning, for example, when the calculated third shift amount is smaller than a threshold value. On the other hand, when the calculated third shift amount is equal to or greater than the threshold value, the bed controller 14 moves the bed 12 by the calculated third shift amount, captures the X-ray fluoroscopic image of the patient again, and the 3D-2D positioning executer 140 executes the 3D-2D positioning processing again using the captured X-ray fluoroscopic image. The process is repeated, and the positioning is finally approved by the radiation therapist.

The series of processes executed by the 3D-3D positioning executer 130 and the 3D-2D positioning executer 140 described above is not limited to positioning before the radiation therapy, and can also be applied to verify the positioning after treatment using the CT image captured after the radiation therapy, for example. Specifically, first, the CT image of the patient is captured by the CT photographing device 16 immediately after the treatment beam B is radiated. Next, the 3D-3D positioning executer 130 performs 3D-3D positioning processing between the captured CT image and the CT image captured in the treatment planning stage. Thereafter, the 3D-2D positioning executer 140 may generate a DRR image based on the shift amount specified through the 3D-3D positioning processing, and perform 3D-2D positioning between the generated DRR image and the X-ray fluoroscopic image at the time of positioning approval. It is possible to verify the positioning using this 3D-3D positioning or the shift amount specified by the 3D-2D positioning. Thus, the "second stage" is a concept including both immediately before the radiation therapy (that is, the treatment stage) and immediately after the radiation therapy.

The display controller 150 causes the display device 200 to display various types of information processed by the medical image processing device 100. For example, the display controller 150 may cause the display device 200 to display the DRR image generated from the second image corrected by the first shift amount and the X-ray fluoroscopic image of the patient together. When the DRR image is generated from the first image, the display controller 150 may also cause the display device 200 to display the DRR image and the X-ray fluoroscopic image of the patient together. Further, for example, the display controller 150 may cause the display device 200 to display an execution result of the 3D-3D positioning processing or an execution result of the 3D-2D positioning processing. Further, for example, the display controller 150 may cause the display device 200 to display an interface (IF) that receives a designation regarding whether to generate the DRR image based on one (or both) of the first image or the second image and execute the 3D-2D positioning processing after execution of the 3D-3D positioning.

Figure 5:
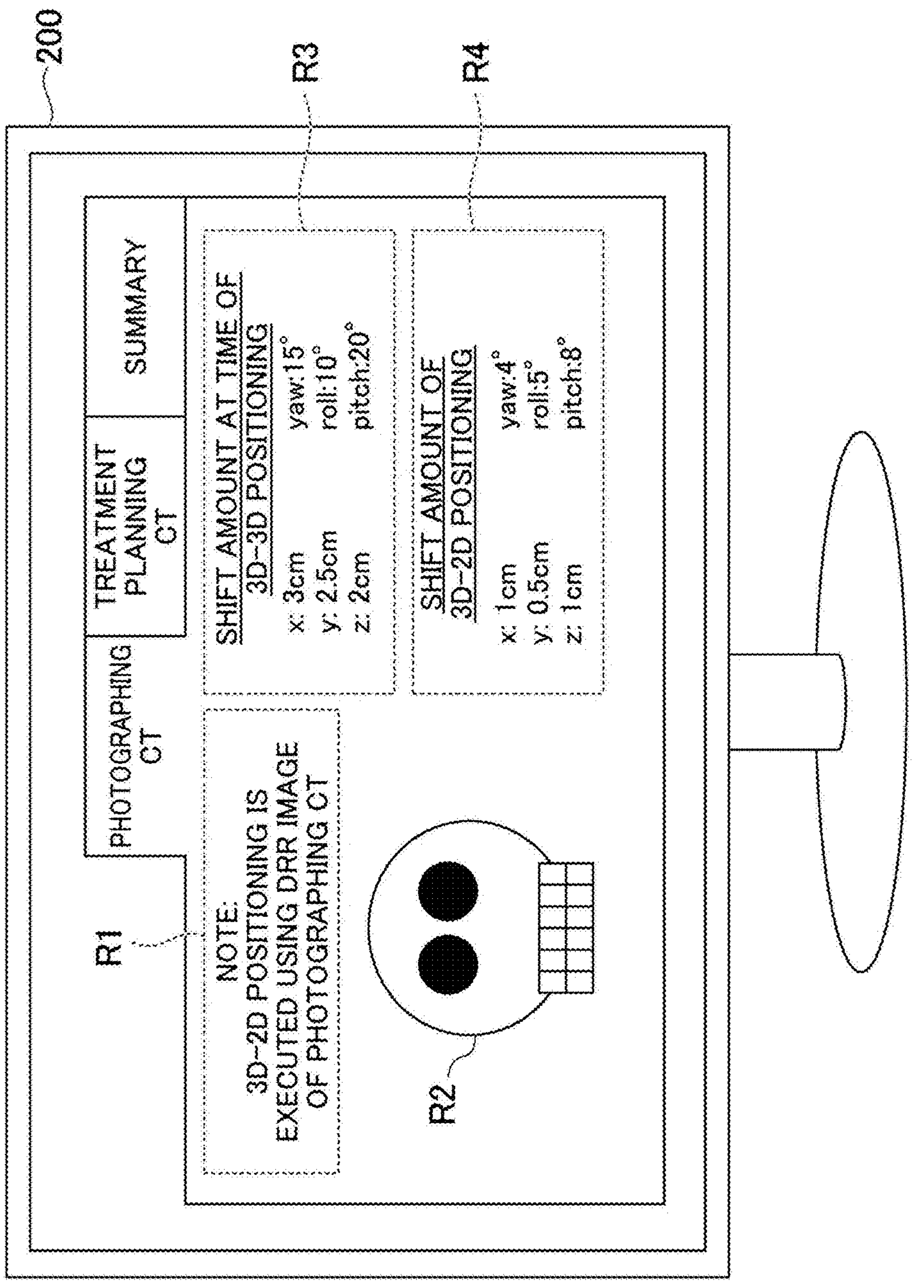
FIG. 5 is a diagram showing an example of an execution result of 3D-2D positioning processing that is displayed by the display device 200.

FIG. 5 is a diagram showing an example of the execution result of the 3D-2D positioning processing that is displayed by the display device 200. In FIG. 5, a photographing CT tab represents the execution result of the 3D-2D positioning processing for collating the DRR image generated from the second image with the X-ray fluoroscopic image of the patient, a treatment planning CT tab represents the execution result of the 3D-2D positioning processing for collating the DRR image generated from the first image with the X-ray fluoroscopic image of the patient, and a summary tab represents summary information of the execution result of the 3D-2D positioning processing. FIG. 5 shows an example in which the execution result of the 3D-2D positioning processing for collating the DRR image generated from the second image with the X-ray fluoroscopic image of the patient is displayed on the display device 200 as a result of the radiation therapist selecting the photographing CT tab. More generally, the display device 200 may display the execution results of the two 3D-2D positioning processing in a switchable manner using any interface such as a button or check box, or may display a plurality of results on one screen simultaneously.

In FIG. 5, a region R1 represents attention-calling information regarding the execution of the 3D-2D positioning processing using the DRR image generated from the second image. Alternatively, for calling attention, the display device 200 may change a color of the DRR image or a color of a frame line thereof shown in the region R2 to call attention to the radiation therapist. A message displayed in the region R1 may be displayed constantly, or may be displayed as a pop-up, for example, at a timing when the DRR image of the photographing CT has been displayed or at a timing when a positioning calculation is executed. Furthermore, after the positioning is approved, a message for calling attention may be displayed again at a timing when a movement amount is transmitted to the bed 12. This makes it possible for the radiation therapist to accurately recognize which DRR image is being used for execution of the 3D-2D positioning processing without any misunderstanding.

A region R3 represents an execution result of the 3D-3D positioning processing performed before the 3D-2D positioning processing is executed. A region R4 represents an execution result of the 3D-2D positioning processing using the DRR image generated from the second image. Thus, the display device 200 displays the execution result of the 3D-3D positioning processing and the execution result of the 3D-2D positioning processing together, thereby making it possible for the radiation therapist to confirm whether the patient has been positioned appropriately.

Figure 6:
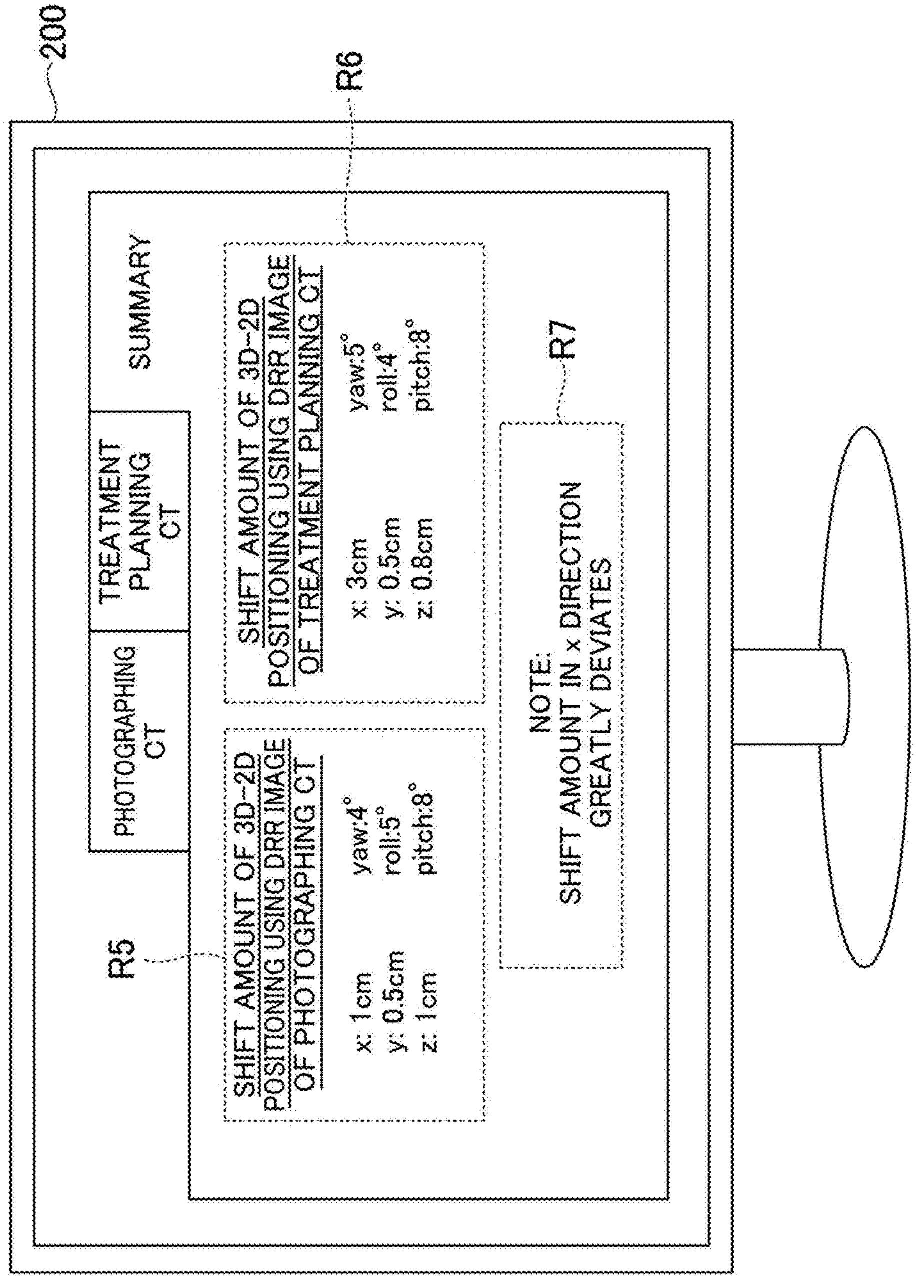
FIG. 6 is a diagram showing another example of the execution result of the 3D-2D positioning processing that is displayed by the display device 200.
Figure 7:
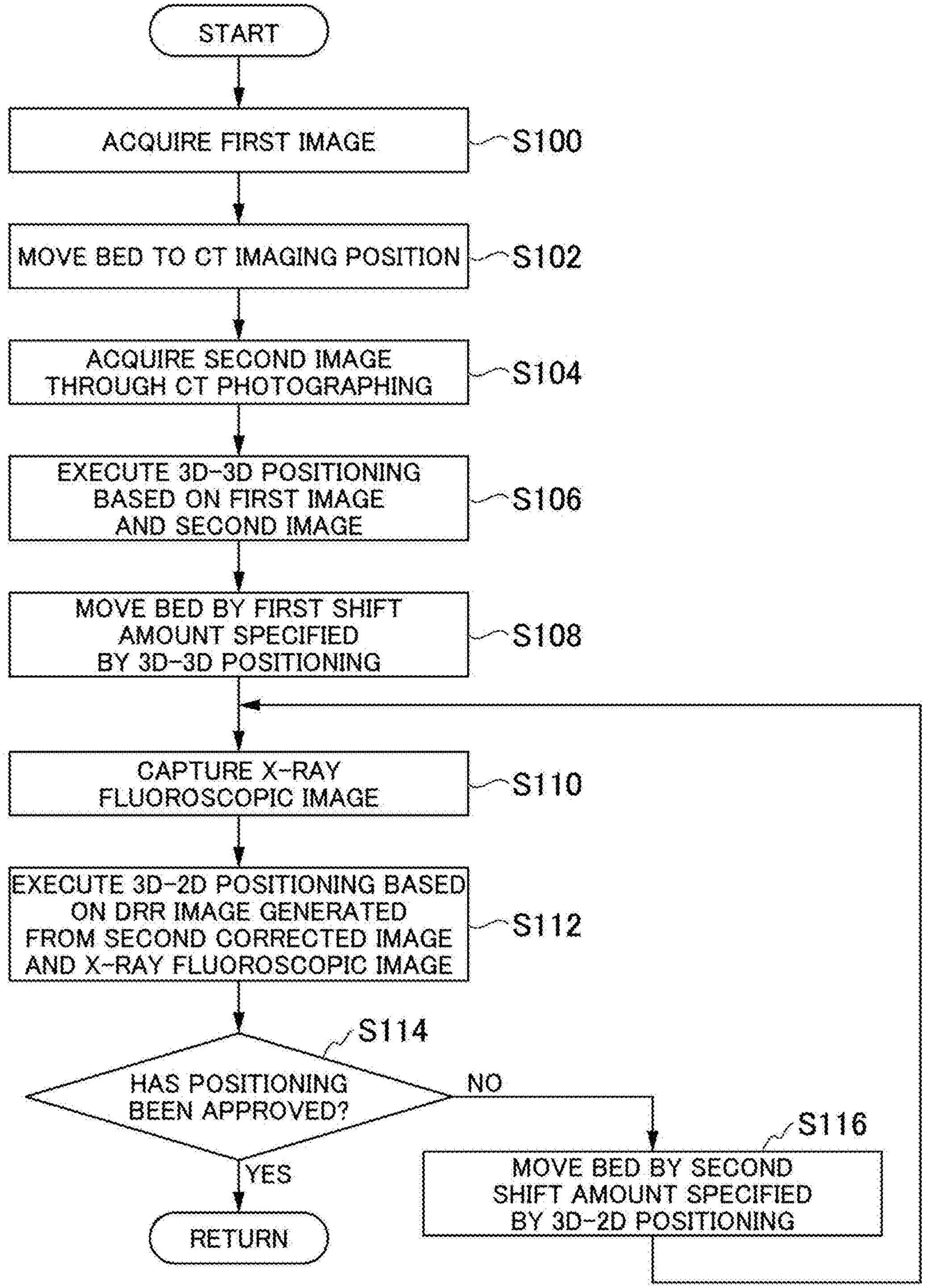
FIG. 7 is a flowchart showing an example of a flow of processing that is executed by the medical image processing device 100 of the embodiment.

FIG. 6 is a diagram showing another example of the execution result of the 3D-2D positioning processing that is displayed by the display device 200. FIG. 6 shows, as an example, a scene in which the radiation therapist selects the summary tab on the display device 200. In FIG. 6, a region R5 represents the execution result of the 3D-2D positioning processing using the DRR image generated from the second image, and a region R6 represents the execution result of the 3D-2D positioning processing using the DRR image generated from the first image. As shown in a region R7, when a deviation between the execution result of the 3D-2D positioning processing using the DRR image generated from the second image and the execution result of the 3D-2D positioning processing using the DRR image generated from the first image is equal to or larger than a threshold value, the display controller 150 causes the display device 200 to display information indicating that the deviation is large. A message displayed in the region R7 may be displayed constantly, or may be displayed as a pop-up, for example, when the calculation of the 3D-2D positioning is completed or at the timing when the movement amount is transmitted to the bed 12. Further, for example, after the message is displayed, a screen for confirming the execution result of the 3D-3D positioning may be automatically displayed. This makes it possible for the radiation therapist to confirm whether the patient has been positioned appropriately. Next, a flow of processing that is executed by the medical image processing device 100 will be described with reference to FIG. 7. FIG. 7 is a flowchart showing an example of a flow of processing that is executed by the medical image processing device 100.

First, the first image acquirer 110 acquires the first image of the patient P captured by the CT photographing device 16 in the treatment planning stage (step S100). Next, the bed controller 14 moves the bed 12 to the CT imaging position (step S102). Next, the second image acquirer 120 acquires the second image of the patient P captured by the CT photographing device 16 in the CT photographing device (step S104).

Next, the 3D-3D positioning executer 130 performs 3D-3D positioning processing for aligning the position of the patient P when the radiation therapy is performed, based on the first image acquired by the first image acquirer 110 and the second image acquired by the second image acquirer 120 (step S106). Next, the bed controller 14 moves the bed 12 by the first shift amount specified through the 3D-3D positioning processing (step S108).

After the bed 12 is moved, the medical image processing device 100 captures the X-ray fluoroscopic image of the patient P using the X-ray photographing device (step S110). Next, the 3D-2D positioning executer 140 performs the 3D-2D positioning processing for calculating the second shift amount between the DRR image generated from the second image corrected by the first shift amount and the X-ray fluoroscopic image (step S112).

Next, the medical image processing device 100 determines whether the positioning has been approved by the radiation therapist (step S114). More specifically, the medical image processing device 100 may determine whether the positioning has been manually approved by the radiation therapist on an interface (IF) on the display device 200, or may automatically determine the approval of the positioning by determining whether the calculated second shift amount is within the threshold value.

When a determination is made that the positioning has been approved by the radiation therapist, the medical image processing device 100 confirms the positioning and ends the processing of this flowchart. On the other hand, when a determination is made that the positioning has not been approved by the radiation therapist, the bed controller 14 moves the bed 12 by the second shift amount specified by the 3D-2D positioning processing (step S116) and returns the processing to step S110 again.

Through the processing of the flowchart, the medical image processing device 100 corrects the second image using the first shift amount specified through the 3D-3D positioning processing, and executes the 3D-2D positioning processing, based on the DRR image generated from the corrected second image and the X-ray fluoroscopic image obtained by photographing the patient P after the bed is moved by the first shift amount. This makes it possible to effectively utilize the CT images captured in the treatment stage for positioning of the patient.

In the processing of the flowchart in FIG. 7, in step S108, the bed controller 14 moves the bed 12 by the first shift amount specified through the 3D-3D positioning processing. However, the processing of step S108 may be omitted, and when the CT photographing device 16 and the treatment beam irradiation gate 18 are installed at positions apart from each other, the processing of step S108 may be processing for moving the bed 12 by an amount obtained by adding the first shift amount to the distance between the CT imaging position and the irradiation position. Further, the processing of step S112 may be omitted, and in this case, the radiation therapist approves the positioning by visually confirming the generated DRR image and the captured X-ray fluoroscopic image in step S114.

Figure 8:
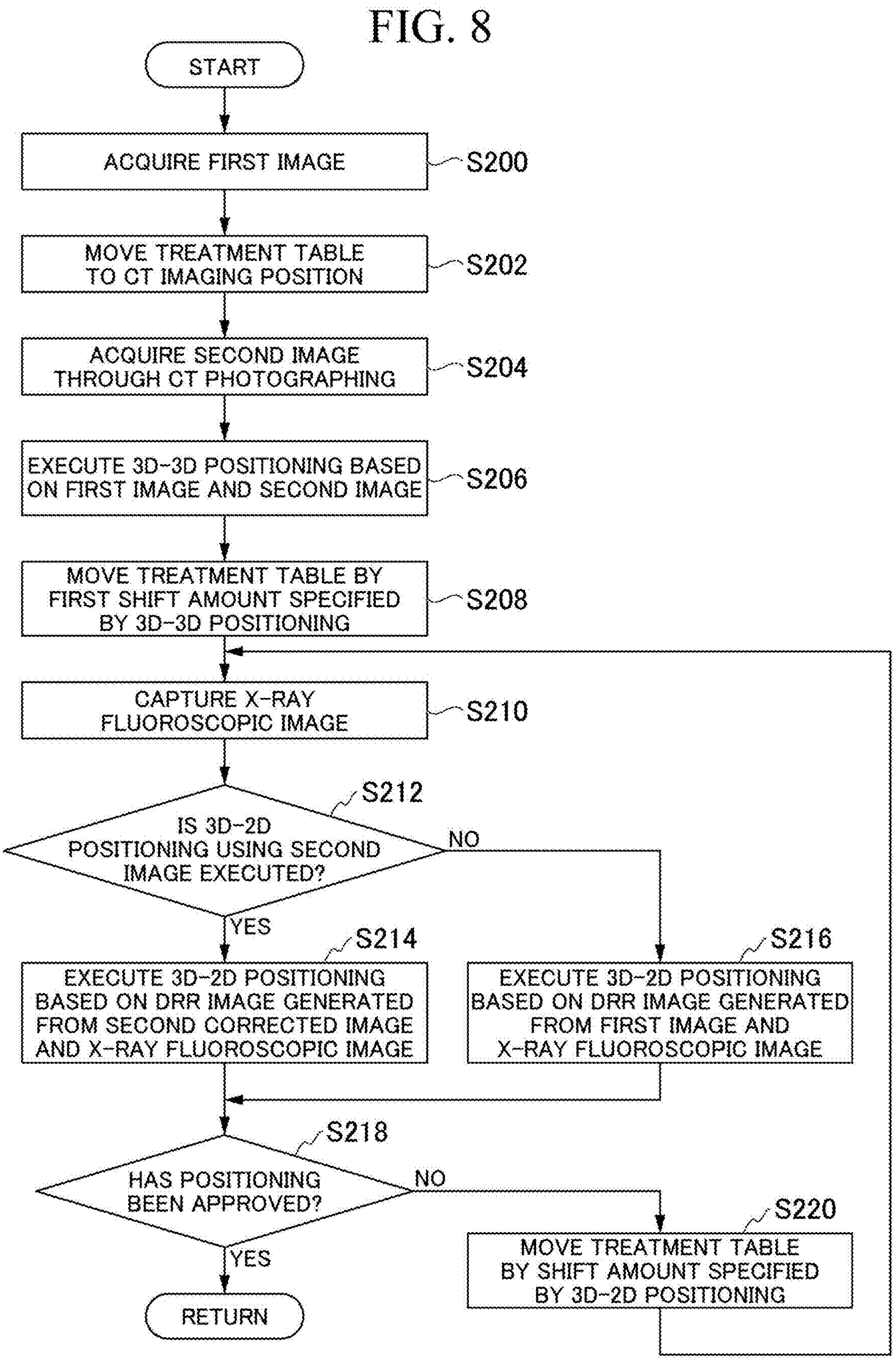
FIG. 8 is a flowchart showing another example of the flow of processing that is executed by the medical image processing device 100 of the embodiment.

Next, a flow of the processing that is executed by the medical image processing device 100 will be described with reference to FIG. 8. FIG. 8 is a flowchart showing another example of the flow of the processing that is executed by the medical image processing device 100.

First, the first image acquirer 110 acquires the first image of the patient P photographed by the CT photographing device 16 in the treatment planning stage (step S200). Next, the bed controller 14 moves the bed 12 to the CT imaging position (step S202). Next, the second image acquirer 120 acquires the second image of the patient P captured by the CT photographing device 16 in the CT photographing device (step S204).

Next, the 3D-3D positioning executer 130 performs 3D-3D positioning processing for aligning the position of the patient P when the radiation therapy is performed, based on the first image acquired by the first image acquirer 110 and the second image acquired by the second image acquirer 120 (step S206). Next, the bed controller 14 moves the bed 12 by the first shift amount specified through the 3D-3D positioning processing (step S208).

After the bed 12 is moved, the medical image processing device 100 uses the X-ray photographing device to capture the X-ray fluoroscopic image of the patient P (step S210). Next, the medical image processing device 100 receives a designation regarding whether or not to the 3D-2D positioning processing using the second image is performed, through the interface (IF) on the display device 200 (step S212). When a determination is made that the 3D-2D positioning processing using the second image is performed, the 3D-2D positioning executer 140 performs 3D-2D positioning processing for calculating the second shift amount between the DRR image generated from the second image corrected by the first shift amount and the X-ray fluoroscopic image (step S214). On the other hand, when a determination is not made that the 3D-2D positioning processing using the second image is performed, the 3D-2D positioning executer 140 performs 3D-2D positioning processing for calculating the third shift amount between the DRR image generated from the first image and the X-ray fluoroscopic image (step S216). In this case, in step S214 and/or step S216, the display controller 150 causes the display device 200 to display the DRR image and the X-ray fluoroscopic image together.

Next, the medical image processing device 100 determines whether the positioning has been approved by the radiation therapist (step S218). More specifically, the medical image processing device 100 may determine whether the positioning has been manually approved by the radiation therapist in the interface (IF) on the display device 200, or may automatically determine the approval of the positioning by determining whether the calculated second shift amount or third shift amount is within the threshold value.

When a determination is made that the positioning has been approved by the radiation therapist, the medical image processing device 100 confirms the positioning and ends the processing of this flowchart. On the other hand, when a determination is made that the positioning is not approved by the radiation therapist, the bed controller 14 moves the bed 12 by the second or third shift amount specified through the 3D-2D positioning processing (step S220), and returns the processing to step S210 again.

Through the processing of the flowchart, the medical image processing device 100 receives a designation regarding execution of the 3D-2D positioning processing using the second image corrected by the first shift amount specified through the 3D-3D positioning processing or execution of the 3D-2D positioning processing using the first image, and determines which 3D-2D positioning processing is executed depending on the designation of the radiation therapist. This makes it possible to improve convenience for the radiation therapist.

In the processing of the flowchart in FIG. 8, in step S208, the bed controller 14 moves the bed 12 by the first shift amount specified through the 3D-3D positioning processing. However, as in the case of the flowchart of FIG. 7, the processing of step S208 may be omitted, and when the CT photographing device 16 and the treatment beam irradiation gate 18 are installed at positions apart from each other, the processing of step S208 may be processing for moving the bed 12 by an amount obtained by adding the first shift amount to the distance between the CT imaging position and the irradiation position. Furthermore, the processing of step S220 may be omitted, and in this case, the processing of step S214 and the processing of step S216 may be executed in a switchable manner.

According to at least one embodiment described above, the medical image processing device 100 corrects the second image using the first shift amount specified through the 3D-3D positioning processing, and executes the 3D-2D positioning processing based on the DRR image generated from the corrected second image and the X-ray fluoroscopic image obtained by photographing the patient P after moving the bed by the first shift amount. This makes it possible to effectively utilize the CT images captured in the treatment stage for positioning of the patient.

While certain embodiments have been described, these embodiments have been presented by way of example only, and are not intended to limit the scope of the inventions. Indeed, the novel embodiments described herein may be embodied in a variety of other forms; furthermore, various omissions, substitutions, and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing device comprising a hardware processor executing a program to implement:

a first image acquirer configured to acquire a first three-dimensional fluoroscopic image, the first three-dimensional fluoroscopic image being a three-dimensional fluoroscopic image of a patient captured in a first stage;

a second image acquirer configured to acquire a second three-dimensional fluoroscopic image, the second three-dimensional fluoroscopic image being a three-dimensional fluoroscopic image of the patient captured in a second stage after the first stage;

a 3D-3D positioning executer configured to execute 3D-3D positioning for calculating a first shift amount between the first three-dimensional fluoroscopic image and the second three-dimensional fluoroscopic image;

a display controller configured to cause a display device to display a first DRR image generated from the second three-dimensional fluoroscopic image corrected based on the first shift amount, and a two-dimensional fluoroscopic image of the patient; and a 3D-2D positioning executer configured to execute 3D-2D positioning for calculating a second shift amount between the first DRR image generated from the second three-dimensional fluoroscopic image corrected based on the first shift amount and the two-dimensional fluoroscopic image of the patient, wherein the display controller is further configured to cause the display device to display information on the second shift amount.

2. The medical image processing device according to claim 1, wherein the display controller is configured to cause the display device to display information on the first shift amount when the 3D-2D positioning is executed.

3. The medical image processing device according to claim 1, wherein the display controller is configured to cause the display device to display information indicating that the second shift amount has been calculated based on the second three-dimensional fluoroscopic image together when the information on the second shift amount is displayed on the display device.

4. The medical image processing device according to claim 1, wherein the 3D-2D positioning executer is further configured to execute 3D-2D positioning for calculating a third shift amount between a second DRR image generated from the first three-dimensional fluoroscopic image and the two-dimensional fluoroscopic image of the patient.

5. The medical image processing device according to claim 4, further comprising:

a receiver configured to receive a designation regarding execution of 3D-2D positioning for calculating the second shift amount between the first DRR image and the two-dimensional fluoroscopic image, or execution of 3D-2D positioning for calculating the third shift amount between the second DRR image and the two-dimensional fluoroscopic image.

6. The medical image processing device according to claim 4, wherein the display controller is configured to cause the display device to display the information on the second shift amount and the information on the third shift amount together, and cause the display device to display information indicating that a deviation between the second shift amount and the third shift amount is large when the deviation is equal to or greater than a threshold value.

7. A treatment system comprising:

the medical image processing device according to claim 1; and a treatment device including an irradiator configured to irradiate the patient with radiation, a first imaging device configured to capture the first three-dimensional fluoroscopic image and the second three-dimensional fluoroscopic image, a second imaging device configured to capture the two-dimensional fluoroscopic image, a bed on which the patient is laid and fixed, and a bed controller configured to perform control to move the bed.

8. A medical image processing method comprising:

acquiring, by a computer, a first three-dimensional fluoroscopic image, the first three-dimensional fluoroscopic image being a three-dimensional fluoroscopic image of a patient captured in a first stage;

acquiring, by the computer, a second three-dimensional fluoroscopic image, the second three-dimensional fluoroscopic image being a three-dimensional fluoroscopic image of the patient captured in a second stage after the first stage;

executing, by the computer, 3D-3D positioning for calculating a first shift amount between the first three-dimensional fluoroscopic image and the second three-dimensional fluoroscopic image;

causing, by the computer, a display device to display a first DRR image generated from the second three-dimensional fluoroscopic image corrected based on the first shift amount, and a two-dimensional fluoroscopic image of the patient; and executing, by the computer, 3D-2D positioning for calculating a second shift amount between the first DRR image generated from the second three-dimensional fluoroscopic image corrected based on the first shift amount and the two-dimensional fluoroscopic image of the patient, wherein the causing, by the computer, the display device to display further causes the display device to display information on the second shift amount.

9. A computer-readable non-transitory storage medium storing a program for causing a computer to:

acquire a first three-dimensional fluoroscopic image, the first three-dimensional fluoroscopic image being a three-dimensional fluoroscopic image of a patient captured in a first stage;

acquire a second three-dimensional fluoroscopic image, the second three-dimensional fluoroscopic image being a three-dimensional fluoroscopic image of the patient captured in a second stage after the first stage;

execute 3D-3D positioning for calculating a first shift amount between the first three-dimensional fluoroscopic image and the second three-dimensional fluoroscopic image;

cause a display device to display a first DRR image generated from the second three-dimensional fluoroscopic image corrected based on the first shift amount, and a two-dimensional fluoroscopic image of the patient; and execute 3D-2D positioning for calculating a second shift amount between the first DRR image generated from the second three-dimensional fluoroscopic image corrected based on the first shift amount and the two-dimensional fluoroscopic image of the patient, wherein the cause the display device to display further causes the display device to display information on the second shift amount.

* * * * *